(12) United States Patent
Lui et al.

(10) Patent No.: US 8,318,955 B2
(45) Date of Patent: Nov. 27, 2012

(54) PROCESS FOR PREPARING 2,4-DIOXOTETRAHYDROFURAN-3-CARBOXYLATES

(75) Inventors: Norbert Lui, Odenthal (DE); Jens-Dietmar Heinrich, Burscheid (DE); Christian Funke, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 161 days.

(21) Appl. No.: 12/854,517

(22) Filed: Aug. 11, 2010

(65) Prior Publication Data

US 2011/0060147 A1   Mar. 10, 2011

Related U.S. Application Data

(60) Provisional application No. 61/232,986, filed on Aug. 11, 2009.

(30) Foreign Application Priority Data

Aug. 11, 2009  (EP) .................................. 09167593

(51) Int. Cl.
*C07D 307/00* (2006.01)
(52) U.S. Cl. ....................................................... 549/318
(58) Field of Classification Search ................... 549/318
See application file for complete search history.

(56) References Cited

U.S. PATENT DOCUMENTS

2010/0190990 A1   7/2010 Lui et al.

OTHER PUBLICATIONS

Altenbach et al. J. Med. Chem. 2006, 49, 6869-6887.*
Khadem et al. Carbohydrate Research (1976), 49, 185-93.*
Berichte D. D.Chem Gesekkschaft, 1911, 44, 1759-1765, Berichte D. D.Chem Gesekkschaft, 1911, 44, 1759-1765.*
Mulholland et al. Journal of Chemical Society, Perkin I, 1225-1231.*
Athanasellis, G., et al., "Novel Short-Step Synthesis of Optically Active Tetronic Acids from Chiral α-Hydroxy Acids Mediated by 1-Hydroxybenzotriazole," *Synlett 10*:1736-1738, Thieme Chemistry, Germany (2002).
Benary, E., "Über die Einwirkung von Halogenfettsäure-halogeniclen auf Malonester", *Berichte der Deutschen Chemischen Gesellschaft*, 44:1759-1765, Aus dem Chemischen Institut der Universität Berlin, Germany (1911).
Campbell, A.C., et al., "Synthesis of (*E*)- and (*Z*)-Pulvinones," *J. Chem. Soc. Perkin Trans. I.* 3:1567-1576, RSC Publishing, United Kingdom (1985)

Mitsos, C., et al., "Synthesis of Tetronic Acid Derivatives from Novel Active Esters of α-Hydroxyacids," *J Heterocyclic Chem.* 39:1201-1205, Wiley-Blackwell, United States (2002).
Mulholland, T.P.C., et al., "A Synthesis of Tetronic Acid [Furan-2(3*H*),4(5*H*)-dione] and Three Analogues," *J. Chem. Soc. Perkin Trans. I.* 9-10:1225-1231, RSC Publishing, United Kingdom (1972).
International Search Report for Application No. PCT/EP2010/004777, European Patent Office, The Netherlands, mailed on Oct. 11, 2010.
English language translation of Benary, E., "The action of halo-fatty acid halides on malonates, II. Synthesis of tetramic acid", *Berichte der Deutschen Chemischen Gesellschaft*, 44:1759-1765, Institute of Chemistry of the University of Berlin, Germany (1911).

* cited by examiner

*Primary Examiner* — Nizal Chandrakumar
(74) *Attorney, Agent, or Firm* — Sterne, Kessler, Goldstein & Fox P.L.L.C.

(57) ABSTRACT

Process for preparing 2,4-dioxotetrahydrofuran-3-carboxylates of the formula (I) and/or (I')

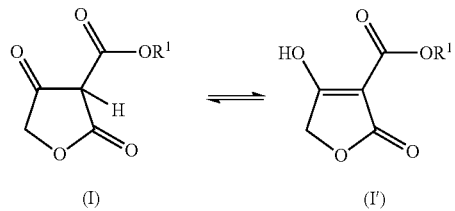

comprising the reaction of a haloacetyl chloride compound of the formula (II)

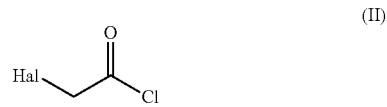

with a malonic ester of the formula (III)

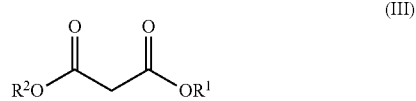

in which Hal, $R^1$ and $R^2$ have the definitions stated in the application, in the presence of a suitable base and optionally in the presence of a solvent; the addition of a sufficient amount of water to the reaction mixture; and the isolation of the desired 2,4-dioxotetrahydrofuran-3-carboxylate.

15 Claims, No Drawings

PROCESS FOR PREPARING 2,4-DIOXOTETRAHYDROFURAN-3-CARBOXYLATES

The present invention relates to a process for preparing 2,4-dioxotetrahydrofuran-3-carboxylates.

2,4-Dioxotetrahydrofuran-3-carboxylates are important intermediates in the preparation of active ingredients. They can be prepared by a variety of known methods.

For example, Athanasellis et al. (Synlett, 2002 (10), 1736-1738) describe a hydroxybenzotriazole-mediated multi-stage synthesis of 3-methoxycarbonyltetronic acids, i.e. 2,4-dioxotetrahydrofuran-3-carboxylates, using O-protected α-hydroxy acids and a malonic ester, with subsequent cyclization in the presence of sodium hydride. The reaction produces elemental hydrogen.

Mitsos et al. (Journal of Heterocyclic Chemistry, 39 (6), 1201-1205) likewise describe the preparation of 2,4-dioxotetrahydrofuran-3-carboxylates. Through an N,N'-dicyclohexylcarbodiimide-mediated condensation reaction of O-protected α-hydroxy acids with N-hydroxysuccinimides, first the N-succinimidyl ester of an α-acetoxy acid is prepared, which then reacts with a dialkyl malonate anion generated by reaction of malonic ester and sodium hydride in anhydrous benzene. The reaction produces elemental hydrogen. The reaction mixture is worked up aqueously and the desired product is obtained by acidification.

The processes described by Athanasellis and Mitsos have the disadvantage that they cannot be used cost-efficiently on an industrial scale. The chemicals used are expensive and the processes are complex, involving numerous steps and at the same time employing sodium hydride. Operating with sodium hydride is generally undesirable, since it is highly flammable and operations must take place with exclusion of water. In addition, the elemental hydrogen that is produced in the reaction must be removed from the reaction system, entailing further process steps and special safety measures.

A process for preparing 3-ethoxycarbonyl-4-hydroxyfuran-2(5H)-one, the cool form of 2,4-dioxotetrahydrofuran-3-ethoxylate, which operates without the use of sodium hydride is described in Campbell et al. (J. Chem. Soc. Perkin Trans 1985, 1567-1576) (Scheme 1).

Scheme 1:

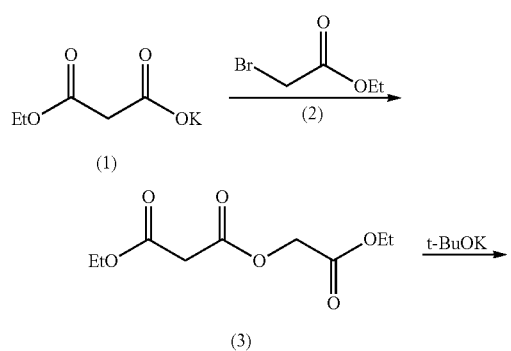

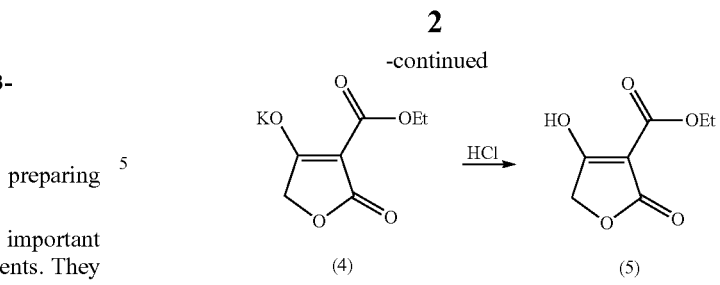

The starting point here, however, is the malonic ethyl ester monopotassium salt (1), which in a first step is reacted with ethyl bromoacetate (2) in boiling ethanol to form ethoxycarbonylmethyl ethyl malonate (3), which then reacts further, additionally, with potassium tert-butoxide in tert-butanol, to form the potassium salt of 3-ethoxycarbonyl-4-hydroxyfuran-2(5H)-one (4). Adding hydrochloric acid in ethanol Rives 3-ethoxycarbonyl-4-hydroxyfuran-2(5H)-one (5). The process is likewise unsuitable for cost-efficient industrial-scale application, since here as well the chemicals used are expensive and the process entails numerous steps.

Similar comments apply to the process described in WO 2009/036899 for preparing 2,4-dioxotetrahydrofuran-3-carboxylates. Here as well, a multi-stage procedure starts from the malonic ethyl ester monopotassium salt and produces the salt of the 3-alkoxycarbonyl-4-hydroxyfuran-2(5H)-one by acylation reaction and subsequent ring closure. Although the chemicals used are less expensive than those employed in the process of Campbell et al., the number of steps in the process is equally high, and this makes industrial-scale application more difficult and/or unprofitable.

A process for preparing ethyl 2,4-dioxotetrahydrofuran-3-carboxylate that operates with fewer steps than the above-mentioned processes, but cannot be employed on an industrial scale, was described by Benary (Benary, Berichte der Deutschen Chemischen Gesellschaft (1911), 44, 1759-1765). In that process the dimethyl malonate used is reacted together with sodium in absolute—i.e. anhydrous—diethyl ether, with liberation of elemental hydrogen, to form the corresponding sodium compound in redox reaction. With ice cooling, chloroacetyl chloride in solution in diethyl ether is then added. The reaction mixture is left then to stand for 24 hours. In addition to the evolution of elemental hydrogen, the use of sodium in anhydrous solvents is not advantageous for industrial-scale application, being too involved and expensive.

On the basis of the known processes for preparing 2,4-dioxotetrahydrofuran-3-carboxylates and/or the corresponding cool tautomers, then, the problem which presents itself is how these compounds can be prepared easily and inexpensively, allowing the process to be used also for the industrial-scale preparation of 2,4-dioxotetrahydrofuran-3-carboxylates. By inexpensive processes are meant those processes which can be carried out without high financial outlay, because, for example, the starting materials are inexpensive and/or unhazardous, the process operates with a few steps or can even be carried out as a "one-pot" reaction, and/or the desired 2,4-dioxotetrahydrofuran-3-carboxylate is obtained in sufficiently high yield and purity.

For the preparation of 2,4-dioxotetrahydrofuran-3-carboxylates, a process has now been found which avoids the disadvantages identified above and which can be carried out easily and inexpensively, particularly since the process found can be carried out in a one-pot reaction and because it operates without expensive and/or hazardous chemicals.

The invention accordingly provides the process described below for preparing 2,4-dioxotetrahydrofuran-3-carboxylates of the formula (I)

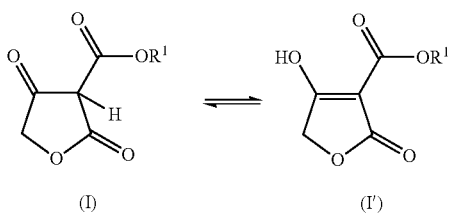

in which $R^1$ stands for the chemical groups defined later on below.

As a result of the keto-enol tautomerism, compounds of the formula (I) may exist in different tautomeric forms. In the context of the present invention, independently of the way in which the compound of the general formula (I) is illustrated, all tautomeric structures of the general formula (I) are encompassed, especially those of the formula (I').

The process of the invention for preparing 2,4-dioxotetrahydrofuran-3-carboxylates of the formula (I) comprises the following steps:
(i) reacting a haloacetyl chloride compound of the formula (II)

in which Hal is bromine, chlorine or iodine, preferably bromine or chlorine, more preferably chlorine, with a malonic ester of the formula (III)

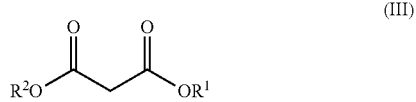

in which
$R^1$ and $R^2$ each independently of one another are $C_{1-12}$ alkyl, $C_{1-12}$ haloalkyl, $C_{5-18}$ aryl, $C_{5-18}$ haloaryl, $C_{7-19}$ alkylaryl or $C_{7-19}$ arylalkyl, or are an alkoxyalkyl of the formula -[A-O]$_m$—B, in which A is $C_{2-4}$ alkanediyl (alkylene), B is $C_{1-6}$ alkyl and m is 1 or 2; preferably $R^1$ and $R^2$ each independently of one another are methyl, ethyl, isopropyl, propyl, benzyl or 2-methoxyethyl, more preferably methyl or ethyl,
in the presence of a suitable base and optionally in the presence of a solvent;
(ii) adding a sufficient amount of water to the reaction mixture; and
(iii) isolating the desired 2,4-dioxotetrahydrofuran-3-carboxylate.

Bases suitable in accordance with the invention are all bases which have the capacity to deprotonate the malonic ester of the formula (III). Bases which are particularly suitable in accordance with the invention are alkoxide bases and have the general formula $X(OR^3)_y$, in which X is an alkali metal cation (e.g. Na$^+$ or K$^+$) or is an alkaline earth metal cation (e.g. Mg$^{2+}$), and $R^3$ is $C_{1-12}$ alkyl, preferably methyl and ethyl, y is 1 if X is an alkali metal cation, and y is 2 if X is an alkaline earth metal cation. Bases according to the invention are, for example, potassium tert-butoxide and sodium methoxide, with preference being given to sodium methoxide on economic grounds.

By sufficient amount of water is meant the amount of water which is sufficient to obtain the desired 2,4-dioxotetrahydrofuran-3-carboxylate of the formula (I) and to isolate this compound from the reaction mixture. The ratio of haloacetyl chloride of the formula (II) to water is preferably in the range from about 1:0.5 to about 1:100, more particularly from about 1:0.8 to about 1:50, especially from about 1:1 to about 1:30. Higher ratios are possible, but are not rational economically.

In step (i) it is preferred in accordance with the invention to heat the malonic ester of the formula (III) either without solvent, i.e. by itself, or in a suitable solvent. Thereafter the base, optionally in solution in a suitable solvent (e.g. sodium methoxide in methanol), is added, and preferably the compound H$_y$(OR$^3$)$_y$ formed and/or the solvent (e.g. methanol) is distilled off at the same time. The base is added commonly at high temperatures, preferably at an internal temperature in the range from about 50° C. to about 250° C., more particularly in the range from about 80° C. to about 150° C. Internal temperatures in the range from about 90° C. to about 150° C. are particularly preferred. The addition and/or the reaction of the compound of the formula (II) with the resultant malonic ester salt takes place preferably at internal temperatures in the range from about 5° C. to about 35° C., more particularly in the range from about 10° C. to about 25° C.

The way in which the desired 2,4-dioxotetrahydrofuran-3-carboxylate of the general formula (I) is isolated from the reaction mixture is arbitrary. Preference is given to filtration and/or phase separation.

2-Haloacetyl chlorides of the formula (II) and malonic esters of the formula (III) are available commercially or can be prepared by known processes.

Preferred malonic esters are those in which $R^1$ is methyl, ethyl, isopropyl, propyl, butyl, allyl, benzyl, alkoxyalkyl or $C_{1-12}$ haloalkyl, more particularly methyl, ethyl, n-propyl or butyl.

Preferred malonic esters are additionally those in which $R^1$ and $R^2$ are the same chemical groups, preferably methyl, ethyl, n-propyl or butyl.

The process of the invention can be illustrated using the following scheme:

Scheme 2:

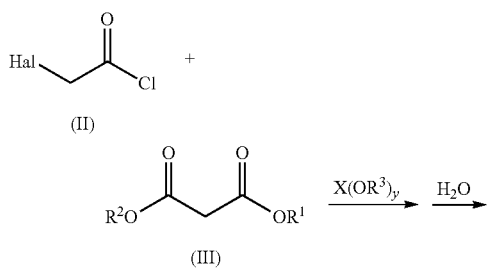

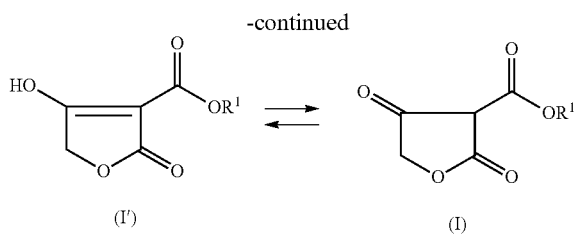

in which Hal, $R^1$, $R^2$, X, $R^3$ and y have the definitions identified above.

The reaction of the malonic ester of the formula (III) with base and subsequently with 2-haloacetyl chloride of the formula (II) can take place in the presence of a solvent or by itself. The reaction is carried out preferably in a solvent. The solvents are used preferably in an amount such that the reaction mixture remains readily stirrable throughout the process. Solvents contemplated for the implementation of the process of the invention include all organic solvents which are inert under the reaction conditions. By solvents in accordance with the invention are also meant mixtures of pure solvents.

Solvents suitable in accordance with the invention are, in particular, ethers (e.g. ethyl propyl ether, methyl tert-butyl ether, n-butyl ether, anisole, phenetol, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, diethylene glycol dimethyl ether, triethylene glycol dimethyl ether, tetrahydrofuran, dioxane, and polyethers of ethylene oxide and/or propylene oxide); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons (e.g. pentane, hexane, heptane, octane, nonane such as the so-called "white spirits" with components having boiling points in the range for example from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene); esters (e.g. methyl, ethyl, butyl, isobutyl acetate, dimethyl, dibutyl or ethylene carbonate, propylene carbonate); amides (e.g. hexamethylenephosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)-pyrimidine, octylpyrrolidone, octylcaprolactam, 1,3-dimethyl-2-imidazolinedione, N-formylpiperidine, N,N'-1, 4-diformylpiperazine) or mixtures thereof.

Preferred solvents used for the reaction according to the invention are aromatic and/or aliphatic hydrocarbons, more particularly xylene, diisopropylbenzene and dichlorobenzene.

As solvent it is possible to use solvents of the invention which can be removed from the reaction mixture by distillation under the reaction conditions of step (i), preference being given to alcohols such as, for example, methanol, ethanol, isopropanol, butanol (i.e. n-butanol, tert-butanol, 2-butanol) and 2-(2-ethoxyethoxy)ethanol. The choice of solvent is dependent on the base used. Where an alkoxide base is used, then preferably the corresponding alcohol is used as solvent.

The process of the invention can be carried out generally in vacuo, at atmospheric pressure or under superatmospheric pressure.

The temperatures employed may vary as a function of the starting materials. The process of the invention can be carried out at temperatures in the range from about 0° C. to about 250° C., preferably at internal temperatures in the range from about 10° C. to about 180° C. The process is preferably carried out under atmospheric pressure; and at internal temperatures in the range from about 20° C. to about 150° C. The reaction with the base can take place at higher internal temperatures, more particularly in the range from about 50° C. to 250° C., and the reaction with haloacetyl chloride of the formula (II) may take place at comparatively low internal temperatures, more particularly at internal temperatures in the range from about 0° C. to about 50° C.

The ratio of the malonic ester of the formula (III) used to the base employed may vary. A significant excess of base, however, should be avoided, since such an excess reduces the yield of the reaction, since the base reacts with the haloacetyl chloride of the formula (II). The ratio of malonic ester of the formula (III) to the base used is preferably in the range from about 1:0.8 to about 1:1.5, more particularly from about 1:0.9 to about 1:1.2, especially from about 1:1 to about 1:1.1.

The ratio of the haloacetyl chloride of the formula (II) employed to the malonic ester of the formula (III) used may vary. A significant excess is not critical for the reaction, but is uneconomic. The ratio of malonic ester of the formula (III) to the haloacetyl chloride of the formula (II) is preferably in the range from about 1:1.8 to about 1:2.5, more particularly in the range from about 1:1.9 to about 1:2.2, especially in the range from about 1:2 to about 1:2.1.

The identification "alkyl" on its own or in combination with other terms, such as arylalkyl, for example, refers to linear or branched, unsaturated hydrocarbon chains having up to 12 carbon atoms, i.e. $C_{1-12}$ alkyl, preferably with up to 6 carbon atoms, i.e. $C_{1-6}$ alkyl, more preferably with up to 4 carbon atoms, i.e. $C_{1-4}$ alkyl. Examples of such alkyls are methyl, ethyl, n- or isopropyl, n-, iso-, sec- or tert-butyl, n-pentyl, n-hexyl, n-heptyl, n-octyl, n-nonyl, n-decyl, n-undecyl and n-dodecyl. The alkyls may be substituted with a suitable substituent.

The identification "aryl"—on its own or in combination with other terms—refers to cyclic aromatic fused or non-fused groups which have 5 to 18 carbon atoms. Preferred aryls have 6 to 14 carbon atoms (e.g. phenyl or naphthyl). Among the aryls, phenyl is particularly preferred.

The identification "arylalkyls" stands for a combination of inventively defined radicals "aryl" and "alkyl", with arylalkyls generally being bonded via the alkyl group. Examples thereof are benzyl, phenylethyl or α-methylbenzyl. Among the arylalkyls, benzyl is preferred.

The identification "alkylaryls" stands likewise for a combination of inventively defined radicals "aryl" and "alkyl", with alkylaryls generally being bonded via the aryl group, such as tolyl, for example.

The identification "alkanediyl" or "alkylene" refers to alkyls as defined above but possessing a further free bonding valency; that is, they possess 2 bonding sites. Examples of such alkanediyls are methylene, ethylene, propylene and cyclopropylene.

"Halogen", "halo" or "hal" is fluorine, chlorine, bromine or iodine, preferably chlorine or bromine.

The present invention is illustrated with reference to the examples below, which do not confine the invention to those examples.

PREPARATION EXAMPLES

Example 1

Dimethyl malonate (200 g, 1.5 mol) in 0.98 kg of xylene is heated to 90° C. Over the course of an hour, 272 g (1.5 mol) of sodium methoxide in methanol are metered in. The methanol liberated is removed by distillation. The jacket temperature is heated to 110° C. (internal temperature 100° C.). Following cooling to 25° C., 284 g of chloroacetyl chloride (30% strength) in xylene are added dropwise with counter-cooling (internal temperature 25° C.). After 3 hours of subsequent stirring at 25° C., 567 g of water are added dropwise. Stirring is then continued at mom temperature, i.e. about 20° C., for a further 3 hours. The organic phase is then separated off and the aqueous phase is concentrated to dryness. This gives 177 g of methyl 2,4-dioxotetrahydrofuran-3-carboxylate (50.6% purity, 44.1% sodium chloride), corresponding to a 74.8% yield.

$^1$H NMR (D$_2$O, 298K) δ: 3.73 (s, 3H), 4.42 (s, 2H)

Example 2

Dimethyl malonate (143 g, 1.05 mol) in 0.77 kg of xylene is heated to 100° C. Over the course of two hours, 180 g (1.00 mol) of sodium methoxide in methanol are metered in. The methanol liberated is removed by distillation. The jacket temperature is heated to 140° C. (internal temperature 125° C.). Following cooling to 15° C., 57.6 g of chloroacetyl chloride are added dropwise with counter-cooling (internal temperature 15° C.). After 3 hours of subsequent stirring at 25° C., 18 g of water are added dropwise. Stirring is continued subsequently at 40° C. for 4 hours, the batch is filtered, and the residue is dried at 40° C. in vacuo. This gives 104 g of methyl 2,4-dioxotetrahydrofuran-3-carboxylate (56.9° A purity as a mixture with NaCl), corresponding to a 74.2% yield.

Example 3

Diethyl animate (50 g, 0.31 mol) in 300 ml of xylene is heated to 110° C. Over the course of 1 hour, 56 g (0.3 mol) of sodium methoxide in methanol are metered in. The methanol liberated is removed by distillation. The jacket temperature is heated to 140° C. (internal temperature 125° C.). Following cooling to 15° C., 17.6 g of chloroacetyl chloride are added dropwise with counter-cooling (internal temperature 15° C.). After 3 hours of subsequent stirring at 25° C., 100 g of water are added dropwise. Stirring is continued subsequently at 40° C. for 4 hours, the batch is filtered, and the residue is dried at 40° C. in vacuo. This gives 42.6 g in the form of a methyl 2,4-dioxotetrahydrofuran-3-carboxylate and ethyl 2,4-dioxotetrahydrofuran-3-carboxylate mixture (46% purity as a mixture with NaCl), corresponding to a 73% yield.

$^1$H NMR (D$_2$O, 298K) for the ethyl ester δ: 1.28 (t, 3H), 3.73 (s, 3H), 4.21 (q, 2H), 4.42 (s, 2H)

The invention claimed is:

1. A process of preparing 2,4-dioxotetrahydrofuran-3-carboxylates of formula (I):

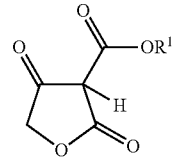

(I)

wherein R$^1$ is C$_{1-12}$ alkyl, C$_{1-12}$ haloalkyl, C$_{5-18}$ aryl, C$_{5-18}$ haloaryl, C$_{7-19}$ alkylaryl or C$_{7-19}$ arylalkyl, or is alkoxyalkyl of the formula -[A-O]$_m$-B, in which A is C$_{2-4}$ alkanediyl (alkylene), B is C$_{1-6}$ alkyl and m is 1 or 2, which process comprises:

(a) reacting a compound of formula (III)

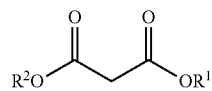

(III)

wherein R$^2$ is selected from the group consisting of C$_{1-12}$ alkyl, C$_{1-12}$ haloalkyl, C$_{5-18}$ aryl, C$_{5-18}$ haloaryl, C$_{7-19}$ alkylaryl or C$_{7-19}$ arylalkyl, or are alkoxyalkyl of the formula -[A-O]$_m$-B, in which A is C$_{2-4}$ alkanediyl (alkylene), B is C$_{1-6}$ alkyl and m is 1 or 2, with a base to give a deprotonated compound,
wherein the base is sodium methoxide (b) reacting the deprotonated compound with a compound of formula (II)

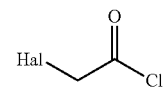

(II)

wherein Hal is selected from the group consisting of chlorine, bromine and iodine; and (c) adding water; wherein the process is effected in one pot.

2. The process according to claim 1, wherein R$^1$ and R$^2$ each independently of one another are methyl, ethyl, isopropyl, propyl and benzyl.

3. The process according to claim 1, wherein the ratio of malonic ester of the formula (III) to the base used is in the range from about 1:0.8 to about 1:1.5.

4. The process according to claim 1, wherein the ratio between haloacetyl chloride and water is in the range from about 1:0.5 to about 1:100.

5. The process according to claim 1, wherein the base is reacted with the compound (III) at an internal temperature in the range from about 50° C. to about 250° C.

6. The process according to claim 1 wherein the compound (II) is reacted at an internal temperature in the range from about 0° C. to about 50° C.

7. The process according to claim 1 further comprising at least one solvent.

8. The process according to claim 7 wherein the at least one solvent has a boiling range of from 40° C. to 250° C.

9. The process according to claim 7 wherein the solvent is xylene.

10. The process according to claim 1 wherein $R^1$ is methyl.

11. The process according to claim 1 wherein $R^2$ is methyl.

12. The process according to claim 1 wherein $R^1$ is ethyl.

13. The process according to claim 1 wherein $R^2$ is ethyl.

14. The process according to claim 1 wherein Hal is chlorine.

15. The process according to claim 1 wherein Hal is bromine.

* * * * *